United States Patent [19]

Smith et al.

[11] Patent Number: 5,057,416
[45] Date of Patent: Oct. 15, 1991

[54] SUPERSECRETING MUTANTS OF SACCHAROMYCES CEREVISIAE

[75] Inventors: Robert A. Smith, Watertown; Margaret J. Duncan, Brookline, both of Mass.

[73] Assignee: Collaborative Research, Inc., Bedford, Mass.

[21] Appl. No.: 273,362

[22] Filed: Nov. 18, 1988

Related U.S. Application Data

[63] Continuation of Ser. No. 843,124, Mar. 27, 1986, abandoned, which is a continuation-in-part of Ser. No. 721,198, Apr. 9, 1985, abandoned.

[51] Int. Cl.$^5$ .................. C12P 21/00; C12N 1/16; C12N 1/18
[52] U.S. Cl. .................. 435/691; 435/69.4; 435/69.8; 435/69.9; 435/212; 435/219; 435/226; 435/320.1; 435/172.3; 435/172.1; 435/255; 435/256; 435/171; 935/47; 935/48
[58] Field of Search .................. 435/68.7, 122.3, 254, 435/255, 256, 320, 172.1, 172.3, 212, 219, 226, 69.1, 69.4, 69.8, 69.9, 171; 935/47, 48

[56] References Cited

FOREIGN PATENT DOCUMENTS

0109560  5/1984  European Pat. Off. .......... 435/69.1
0121884 10/1984  European Pat. Off. .......... 435/69.1
0128743 12/1984  European Pat. Off. .......... 435/69.1

OTHER PUBLICATIONS

Sherman et al. *Methods in Yeast Genetics* pp. 3–8, 1982, "Isolation and Characterization of Auxotrophic, Temperature-Sensitive and UV-Sensitive Mutants".

Current Genetics, vol. 7, No. 1, 1983 Berlin, Heidelberg, N.Y., H. Bussey et al., "Protein Secretion in Yeast: Two Chromosomal Mutants that Oversecrete Killer Toxin in *Sccharomyces cerevisiae*" pp. 449–456, pp. 449, column 1, summary, p. 456, column 1, line 3–12.

*Primary Examiner*—Robin L. Teskin
*Attorney, Agent, or Firm*—Wolf, Greenfield & Sacks

[57] ABSTRACT

A screening procedure is provided which utilizes a milk clotting assay for selecting supersecreting yeast cells for obtaining high yields of desired polypeptide products.

Supersecreting yeast cells are provided as filed with American Type Culture Collection.

Final polypeptide products are obtained from mutant yeast strains which have been screened as to secreting properties with supersecreters then cultured to obtain high yields.

22 Claims, 2 Drawing Sheets

SUPERSECRETING MUTANTS OF SACCHAROMYCES CEREVISIAE

This application is a continuation of application Ser. No. 6,843,124, filed 3/27/86, now abandoned, which is a continuation-in-part of U.S. application Ser. No. 6,721,198, filed 4/9/85 now abandoned.

BACKGROUND

Recent developments in recombinant DNA technology allow one to express genes from higher organisms in bacteria and yeast, which can be grown in large scale fermentations. This technology has spawned a number of efforts to develop commercially viable fermentation processes in which these microorganisms produce proteins such as enzymes or hormones, which must otherwise be isolated from animal or human tissue. In many cases much of the cost of such fermentative processes is in the steps required to recover the desired product in an acceptably pure state. Usually, the microorganisms must be disrupted, and their contents solubilized with denaturants before the desired product can be isolated and purified away from other cell components. Each processing step adds to the final cost of the product.

One way to avoid such a lengthy purification procedure is to arrange for the microorganism to secrete the desired product directly into its growth medium during fermentation. In this way the product can be obtained immediately, in a relatively pure form, simply by removing the producing cells in a single centrifugation or filtration step.

The yeast *Saccharomyces cerevisiae* has often been put forward as the microorganism of choice for secretory production of protein products. Because it has been used for centuries in the baking and brewing industries, much is known about growing this species on a large scale. Also, it is known to be capable of secreting a significant portion of the protein it produces.

However, previous attempts to use *Saccharomyces cerevisiae* to produce and secrete protein products from heterologous genes have had mixed success. The secreted yield of protein product was dependent upon both the gene to be expressed and the promoter and signal sequences chosen for its expression (Hitzeman, R. A., Leung, D. W., Perry, L. J., Kohr, W. J., Levine, H. L. and Goeddel, D. V. (1983) Science 219, 620–625; Bitter, G. A., Chen, K. K., Banks, A. R. and Lai, P.-H. (1984) Proc. Natl. Acad. Sci. USA 81, 5330–5334; Brake, A. J., Merryweather, J. P., Coit, D. G., Heberlein, U. A., Masiarz, F. R., Mullenbach, G. T., Urdea, M. S., Valenzuela, P. and Barr, P. J. (1984) Proc. Natl. Acad. Sci. USA 81, 4642–4646; Brake, A. J., Cousens, L. S., Urdea, M. S., Valenzuela, P. D. T. (1984) European Patent Application Publication No. 0 121 884). Although it is usually possible to obtain reasonably good production levels for a particular protein, often only a small fraction of the total amount produced can actually be found free in the medium. Most of the protein remains trapped inside the cell, often in the intracellular vacuole found in this species. In yeast, secretion can be regarded as a branched pathway with some secreted yeast proteins being "secreted" into the vacuole and others being directed across the plasma membrane to the periplasm and beyond (Sheckman, R. and Novick, P., in Strathern, J. N., Jones, E. W. and Broach, J. R. (eds.), Molecular Biology of the Yeast *Saccharomyces cerevisiae*, Cold Springs Harbor Laboratory, Cold Springs Harbor, New York, 1981, pp. 361–398). Apparently, some protein products of foreign genes are directed into the vacuolar branch of this pathway.

Recent studies by Rothstein, J. H. and Stevens, T. H. (Presentation at the Genetics Society of America Annual Meeting, Aug. 13, 1984) and Emr, S. (Presentation at Yeast Expression Vectors Symposium, Banbury Center, Cold Spring Harbor Laboratory, Jun. 21—24, 1984) have shown that host cell mutations can be isolated that affect the intracellular localization of yeast proteins in the yeast secretion pathway. Both a natural yeast protein (carboxy peptidase Y) and a fusion of two yeast proteins (carboxy peptidase Y and invertase) were redirected from the vacuole to the outside of the cell by host cell mutagenesis and selection. However, the utility of using the mutant strains generated by either of these selection methods for the secretory production of foreign proteins has not been demonstrated. Furthermore, in each case a strong selective pressure for the extracellular secretion of a specific protein was applied to the mutagenized cells. This approach differs greatly from a quantitative screening assay for a nonessential gene product and may have introduced strong bias in the distribution of mutants obtained. Also, neither of these studies were directed at increasing the yield of secreted proteins per se, rather they were designed to isolate mutations to aid in the general study of yeast secretion.

One group has reported an attempt to isolate mutant stains of yeast that oversecrete the killer toxin which is associated with some yeast strains (Bussey, H., Steinmetz O., and Saville, D. (1983) Current Genetics, 7:449–456). However, this group succeeded only in isolating chromosomal mutations that reduced the rate of toxin proteolysis, or reduced the amount bound to the cell wall of producing cells. The actual translocation of this polypeptide in the yeast secretion pathway was unaffected.

SUMMARY OF THE INVENTION

It is an object of the present invention to provide mutant yeast cells which have an increased capacity for secreting polypeptides such as proteins.

It is a further object of this present invention to create a method for screening mutant yeast cells to determine those which have an increased capacity for secreting polypeptides such as proteins.

Another object of the present invention is to provide a method for the production of a heterologous polypeptide such as a protein by means of secretion from a yeast cell transformed with all or part of a recombinant plasmid carrying the gene for a heterologous polypeptide such as a protein.

It is an additional object of the present invention to provide mutant strains of *Saccharomyces cerevisiae* which produce and secrete heterologous polypeptides such as proteins.

It has now been found that mutant strains of yeast can be obtained that have the ability to secrete heterologous polypeptides such as proteins with high efficiency. Upon expression of the protein product within the yeast cell, the expressed product is processed, if necessary, and then transported into the medium of the cell culture.

According to the invention, a desired final polypeptide product such as a mature protein, is obtained in high yields from supersecreting yeast cells by collecting the polypeptide products secreted from the yeast cells. The yeast cells are obtained by selecting a starting transformable yeast strain and causing the yeast strain to undergo mutagenesis and form mutant cells or to allow spontaneous mutant to form. The mutant cells are transformed to secrete a heterologous polypeptide. The mutant cells are then screened to determine those final cells which secrete the last mentioned heterologous polypeptide in amounts greater than two times the amounts secreted by the starting strain when so transformed. The final cells obtained are cultured to obtain high yields of the heterologous polypeptide. The final cells can be cured of the recombinant plasid prior to culturing, and transformed again with a gene which gives the final desired polypeptide product, or not cured, but additionally transformed with the gene for another polypeptide. In some cases, the gene with which the original strain is transformed is such as to produce the final desired polypeptide products in the supersecreting mutants.

The mutant cells discussed above can be transformed prior to mutagenesis or after mutagenesis.

In a preferred form, the polypeptide is prochymosin because its expression and secretion is capable of being simply and efficiently measured in a screening assay to identify the supersecreting mutants resulting from the mutagenesis. *Saccharomyces cerevisiae* is the preferred yeast species transformed. The yeast strain is provided with DNA sequences for expression and secretion as most desirable for the gene introduced into the strain. A second transformation step or mating to another transformed strain preferably introduces a gene capable of causing secretion of the final desired heterologous polypeptide, which is preferably a mature protein.

Mutant yeast strains are provided which are supersecreting strains for desired final polypeptide products, in that they have a higher capacity for the secretion of heterologous polypeptides or proteins, than often occurs in yeast strains. Surprisingly, the strains are supersecreting for desired products whether or not the expression levels of the products are generally the same as the original strains from which the supersecreting strains are derived.

A screening method is provided which selects a supersecreting yeast strain. The method involves spreading yeast cells on a solid nutrient support plate and allowing growth of individual colonies which have been transformed with the gene for prochymosin. The visible growth is removed from the support and a casein containing solution is applied in a solidifying material as an overlay. The casein containing solution is preferably milk and the solidifying material is preferably agarose. Following incubation, clot formation is noted and the cells producing such clots are recovered for use as supersecreting yeast strains.

A screening method in accordance with the invention preferably goes through the transformation, mutagenesis, and selection steps as described above. After selection, the supersecreting strains can be cured and again transformed or, in some cases, the product used which facilitated an efficient screening method is the final desired product, and no further transformation is required.

Specific supersecreting strains of *Saccharomyces cerevisiae* found to be particularly desirable for obtaining various mature proteins or polypeptides, include strains deposited as American Type Culture Collection accession Numbers 20750, 20751 and 20752 deposited Apr. 5, 1985. As referred to in this specification, such strains are meant to include cells in which the prochymosin gene is replaced with other known genes for producing polypeptides and specific mature protein products. Thus, conventional techniques and methods can be used to further transform the strains on deposit for production of particular designed polypeptides. Surprisingly, strains which secrete a particular polypeptide product at high levels are found to produce other polypeptide products at high levels when provided with required DNA segments.

It is a feature of this invention that the methods herein described can be simply carried out, using known laboratory equipment, to provide high yield of desired polypeptide, and specific mature protein products, from yeast strains that have ordinarily lower production capacity, because they secrete less than the mutants, even though they may express as much product as the mutants. It is a further feature of this invention that particularly desirable high secreting yeast strains are obtained, and are useful, when properly transformed to produce a multitude of different polypeptide products.

Although prochymosin is particularly desirable as a gene product for use as in screening to enable supersecreting cells to be identified, in many cases, products other than prochymosin are desired. In such cases, the selected supersecreting strains can be cured as known by selecting from the supersecreting cell population those cells that no longer retain the prochymosin genetic material. The selected, so cured, cells can then be further transformed by known transforming methods as used for the initial transformation including, but not limited to, the lithium chloride method as described by Ito, H., Fukuda, Y., Murata, K. and Kimura, A. (1983) J. Bacteriol. 153, 163–168, and the spheroplast method as described in *Methods in Yeast Genetics* Laboratory Manual, Sherman, F., Fink, G. R. and Hicks, J. B. (1981) Cold Spring Harbor Laboratory, Cold Spring Harbor, N. Y., or by mating them to other transformed strains.

Separation of the final desired product from the media in or on which the finally transformed supersecreting cells grow, can be carried out by known methods. For example, the culture media can be physically separated from the cells in the case of liquids and treated by filtering, column separation or the like depending upon the final product desired.

BRIEF DESCRIPTION OF THE DRAWINGS

The above and other features of the invention will become apparent to those skilled in the art from the following description, taken in connection with the accompanying drawings wherein.

DESCRIPTION OF THE PREFERRED EMBODIMENTS

Figure 1A:
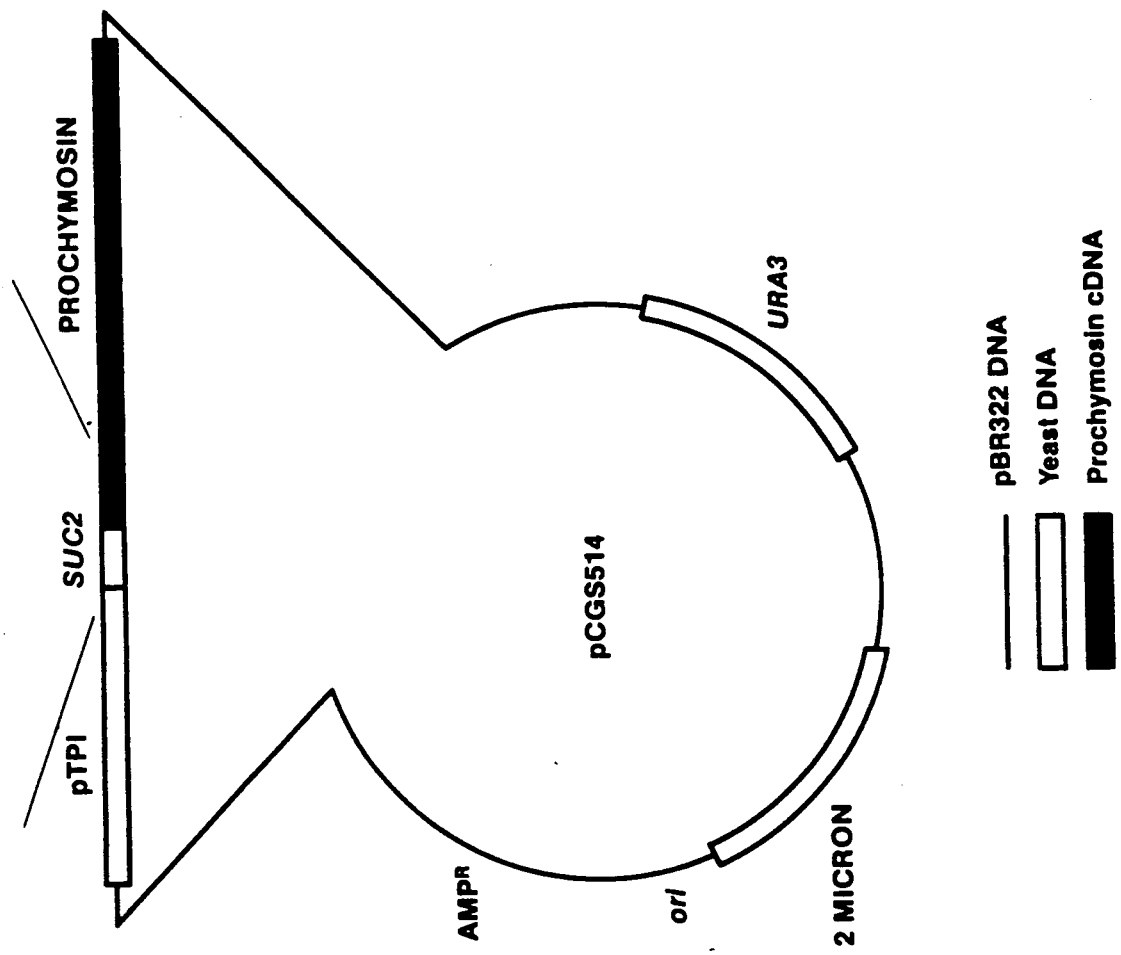
FIGS. 1A and 1B show the structure of the recombinant DNA plasmid pCGS514 is shown including the relative positions and the sources (bacterial plasmid DNA, yeast DNA, and complementary DNA) of the various segments that comprise this plasmid, and the nucleotide sequence of portions of some of these segments is also shown.

As used herein, the following terms have their known meaning in the art defined below:

Mutagenesis as used herein means treatment of a yeast cell with either a known mutagen such as a chemical or radiation, or introduction of new DNA materials into a yeast cell, any of which induces a genetic change.

Mutant yeast cell as used herein means the yeast cell that is the result of a genetic change.

Secretion as used herein means the transport of a polypeptide or protein product through the plasma membrane alone or additionally through the cell wall of the yeast into the surrounding medium.

Secretion signal sequence as used herein means a sequence of hydrophobic amino acid residues attached to the amino terminus of a polypeptide which are essential for the precursor polypeptide to be processed, and the mature protein to be translocated in the secretion pathway of the cell. Alternatively, secretion signal sequence may refer to the DNA sequence that encodes this sequence of amino acid residues. This DNA sequence is located between the translation initiation codon (ATG) and the coding region for the mature form of the polypeptide.

Processing as used herein means (a) the loss or proteolytic cleavage of the signal sequence from the polypeptide or protein so as to produce the polypeptide or protein in mature form; and/or (b) the addition of oligosaccharide to the glycosylation recognition sequences which are inherently present or may be provided by added glycosylation sequences in the mature protein.

Mature protein as used herein means that form of the protein product which is actually secreted by the cell.

Precursor (of a polypeptide or protein) as used herein means a polypeptide or protein as synthesized within a cell having a signal sequence attached to the mature form of the protein. The attendant processing of the precursor results in its mature polypeptide or protein.

Curing refers to a process which eliminates all copies of a plasmid from a yeast strain.

Transformable yeast strain means yeast cells into which foreign DNA can be introduced.

The level of secretion of a protein is regulated inter alia by its host strain and by the specific DNA sequences expressing that protein. After yeast cells, which normally secrete very low levels of the internally produced protein product, are mutagenized, mutant strains can be selected which have a secretion efficiency which is at least two fold higher than the non-mutant strain and such mutant cells are considered to be "supersecreting".

The use of "supersecreting" strains for the secretory production of gene products from yeast is advantageous in those cases wherein polypeptides whose precursors contain signal sequences are produced, but sometimes inefficiently secreted, when the genes for these proteins are expressed in yeast. Examples of such proteins include but are not limited to prochymosin, bovine growth hormone (BGH), proinsulin, prourokinase (PUK), alpha- 1-antitrypsin, tissue plasminogen activator (TPA), interleukin-2 (IL-2) and human growth hormone (HGH).

Yeast strains prepared by the genetic processes described herein are exemplified by cultures now on deposit with the American Type Culture Collection, 12301 Parklawn Drive, Rockville, Md. These cultures are identified by Accession Number 20750, Strain Designation CGY1285, Accession Number 20751, Strain Designation CGY1083, Accession Number 20752, Strain Designation CGY1291, and Accession Number 20753, Strain Designation CGY998 and were deposited by Collaborative Research, Inc. on Apr. 5, 1985.

As more fully described below, the strains to be mutagenized in the present invention can be any strain of yeast that can be transformed with DNA and has or can be transformed to have the appropriate genetic markers to enable one to select transformants. For recognition as a supersecreting strain, it contains or can be transformed to contain DNA sequences required for the expression and secretion of the desired gene product. After the yeast strain is mutagenized, a screening method is required so that those strains which are newly found to be "supersecreting" strains can be isolated away from those strains which are not.

Mutagenesis can be carried out as known in the art by treatment with any of a number of known chemical mutagens including ethyl methane sulfonate (EMS), and nitroso guanidine. The strain or a mixed group of strains can also be mutagenized by treatment with radiation that damages DNA such as ultraviolet light, x-rays or particle radiation. Mutagenesis can also occur by the introduction of new DNA materials. Such DNA materials could include fragments of yeast DNA carried on high copy number plasmid vectors. The variation in these DNA changes could be new combinations of promoter and/or secretion signal sequences with a desired gene, or they could be newly created junctions between segments of DNA such as those created by digestion with a given restriction endonuclease followed by limited digestion with an exonuclease and treatment with DNA ligase. Alternatively, these variations could be newly introduced changes in the DNA sequence of the promoter/secretion signal sequence/gene sequence that have been introduced by any of a variety of in vitro mutagenesis techniques (Shortle, D., Dimaio, D. and Nathans, D. (1981) Ann. Rev. Genetics 15, 265-294). A large number of newly created changes in the yeast DNA can be introduced into the yeast strain to be mutagenized in one transformation experiment.

Once having used any effective mutagenesis treatment to obtain a collection of different mutant cells, a screening method is carried out to identify and isolate the desired mutant cells. The screening method of the present invention relies upon the presence of both a foreign gene to be expressed and the DNA sequences required for its expression and secretion. The gene product should be a material capable of being assayed. In the present invention, the gene is preferably prochymosin along with DNA sequences that allow for its expression and secretion from yeast. Such DNA sequences include a promoter sequence such as the 5' flanking region from the yeast triose phosphate isomerase gene (TPI), or a similar region from another yeast gene such as phosphogycerate kinase (PGK), galactokinase (GAL1), alcohol dehydrogenase (ADH1) or invertase (SUC2). A secretion signal sequence (also known as a "pre" sequence) is also provided which could be the coding region for the amino terminal portion of a secreted yeast gene such as invertase, acid phosphatase or mating factor alpha. Such a secretion signal sequence could also be a similar functioning sequence from a non-yeast gene such as the "pre" sequence of prochymosin, a synthetic "pre" sequence or a "pre" sequence created by combining parts of two or more known "pre" sequences.

Following mutagenesis of the prochymosin producing yeast strain, the mutagenized yeast cells are grown on agar plates. The plates can be made with any of a number of media normally used for the culturing of yeast. It is preferable to use a medium such as "SD"

medium as described in *Methods in Yeast Genetics* Laboratory Manual, Sherman, F., Fink, G. R. and Hicks, J. B. (1981) Cold Spring Harbor Laboratory, Cold Spring Harbor, N. Y., that has a limited ability to regulate the acidity of a growing yeast culture so as to allow the pH near the yeast colonies to drop in the later part of the growth period. This facilities the conversion of prochymosin (the actual secreted product of the strain) to chymosin (the active form of the enzyme) and eliminates the need for an activation step.

Cells are preferably spread on the nutrient agar plates at a density that results in the growth of from 1 to 10 colonies per cm$^2$, but greater densities could be used to advantage in certain cases. After innoculation, the plates are incubated at 20° C. for from 48 to 96 hours, although temperatures as low as 15° C. or as high as 37° C. could be used in some cases. The latter temperatures would be used when it is desirable to isolate or test for mutations which are sensitive to high or low temperature. However, altering the temperature away from the 30° optimum will usually increase the time required for growth.

The yeast cells are removed from the agar medium plates by application of sterile discs made of absorbent material such as filter paper to the surface of the agar medium where the cells are growing. The process is repeated until all the visible cells are removed. The first disc from each plate is preferably stored in a sterile petri dish for later recovery of mutant cells.

At this point it is desirable to assay the amount of active chymosin present in regions of the nutrient agar plate that formerly lay just under the yeast colonies. In conventional practice, chymosin activity is assayed by introducing a sample of the material to be tested into a specific volume of milk and noting the time required for that milk to coagulate or form a clot. However, in the case of a solid surface on which small areas are to be assayed, it is preferable to apply milk to that surface directly. The volume of milk acted upon by each small region can be effectively limited by mixing the milk with an agent such as molten agarose which will cause it to solidify soon after being applied to the surface. Clotted milk can be visualized as opaque regions in the normally translucent milk/agarose mixture.

Thus, a milk agarose overlay containing molten agarose, nonfat dry mil, $CaCl_2$, $NaPO_4$ and pepstatin is poured onto the surface of each plate and allowed to solidify. Pepstatin, a protease inhibitor, is included in the overlay mixture to enable one to screen for mutants with various background strains and DNA constructions that have a range of secreted activities before mutagenesis. Without pepstatin, intense regions of opacity quickly form over colonies that secrete as little as 0.1 units of clotting activity per gram wet weight of cells. With pepstatin, the chymosin activity is partially inhibited and the opaque regions forming over non mutant colonies are much less intense and take several hours to form, thus allowing mutant colonies to be identified. The amount of pepstatin used which can vary from 0 to 100 mg/ml, depends upon the background level of secreted activity to be inhibited and the desired level of secreted activity to be found in the mutants. The concentration of nonfat dry milk can also vary from 2% to 20% w/v or more depending upon the intensity of the opaque region desired and the time for such a region to form.

Each of the plates containing a milk agarose overlay are preferably incubated t room temperature (25° C.) but the range of incubation temperature may be as broad as 0° C. to 40° C. As soon as the first opaque regions of clotted milk are observed, their positions are noted, as these are likely to correspond to those colonies which have secreted the most chymosin. The incubation step is continued until at least faint clots have formed over the regions of the plate corresponding to most of the colonies. This background of faint clots enables one to orient the filter paper replicates with respect to the nutrient agar plates facilitates the identification of colonies on the filter paper replicates that correspond to clots that formed quickly or that were particularly large or intense.

After cells from colonies that correspond to intense or quickly forming clots are streaked out on nutrient agar plates and incubated until individual colonies form, several independent colonies from each putative mutant strain are assayed for secreted chymosin activity. This is done in a number of ways, but it is preferable to use a rapid method that allows one to assay a large number of strains in a reasonably short period of time. One method is to use cells from an isolated colony to innoculate a patch on a nutrient agar plate and incubate that plate until a dense patch of growing yeast is apparent. Cells from this patch are then suspended in buffer and incubated on ice. A sample of this suspension is then added to a specific volume rehydrated nonfat dry milk and incubated with shaking at 30° C., noting the time required for the milk to coagulate. The secreted activity of a strain is calculated by dividing a constant by the product of the time required for coagulation and the number of cells used.

This measurement is preferably performed on at least three colonies from each putative mutant strain and the results averaged to get an accurate measurement of the secreted activity of that strain. An arbitrary cutoff is normally defined at an activity level above which a strain can be considered to have a supersecreting phenotype. For purposes of this invention, this cutoff is defined as two times the secreted activity of the unmutagenized backgound strain.

After a number of supersecreting strains have been identified it is customary to subject them to a variety of genetic analyses to determine the type of mutation that has occurred. Standard techniques of yeast genetics and the quantitative assay described above can be used to determine if the supersecreting phenotype of a given strain is the result of a single mutation, if that mutation is dominant or recessive, the chromosomal location of different mutations, and whether or not various pairs of recessive mutations will complement each other. It is also possible to mate supersecreting strains to unmutagenized strains and sporulate the resulting diploid strains in order to obtain supersecreting strains that do not contain a number of uncharacterized mutations that may effect cell growth (i.e. move the supersecreting mutations into different genetic backgrounds). Further, it is also possible to mate supersecreting strains containing mutations in different complementation groups to each other, and sporulate the resulting diploids in order to isolate multiply mutant strains that contain more than one supersecreting mutation. Often such multiply mutant strains will secrete prochymosin or other heterologous proteins even more efficiently than singly mutant strains. It is also possible to transform super secreting strains with additional recombinant sequences that contain other promoter/signal sequence/gene combinations, either after the resident plasmid has been removed, or in addition to it. A supersecreting strain isolated by this method can also be used as a starting strain for additional rounds of mutatgenesis and screening as described herein.

EXAMPLE 1

In a first example of this invention yeast strain CGY998, which was deposited with the American Type Culture Collection, 12301 Parklawn Drive, Rockville, Md., on Apr. 5, 1985, and is identified by Assession Number 20753, was used as a starting strain. CGY998 is background strain CGY339 (mating type alpha, his4-29, ura3-52, pep4-3) containing the plasmid pCGS514 which is shown in Table 1. This plasmid was derived from the yeast/*E. coli* shuttle vector pCGS40 which has been described by Goff, C. G., Moir, D. T., Kohno, T., Gravius, T. C., Smith, R. A., Yamasaki, E. and Taunton-Rigby, A. (1984) Gene 27, 35-46. pCGS40, was in turn, derived from the well known bacterial plasmid pBR322, and contains the gene for ampicillin resistance (AmpR) and the origin of repication (ori) from this plasmid so that it can be propagated in *E. coli*. Propagation in yeast is assured by the inclusion of the yeast URA3 gene as a selectable marker and an origin of replication from the yeast two micron plasmid (Broach, J. R. and Hicks, J. B. (1980) Cell 21, 501-508). In pCGS514 the region of pBR322 DNA between the cleavage sites for the restriction endonucleases EcoR1 and SalI have been replaced by approximately 2100 base pairs of DNA that is comprised of the following segments of DNA in order: approximately 850 base pairs from the 5' flanking region of the yeast triose phosphate isomerase gene (pTPI) as described by Alber, T. and Kawasaki, G. (1982) J. Mol. Appl. Genet. 1, 423-451, that promotes RNA transcription of adjacent sequences; a 15 base pair synthetic DNA adapter; 79 base pairs from the yeast SUC2 gene (Taussig, R. and Carlson, M. (1983) Nucleic Acids Res. 11, 1943-1954) that, along with the adapter, encodes the amino terminal region of invertase, including its secretion signal sequence; and the entire complementary DNA (cDNA) sequence for prochymosin including an additional amino terminal methionine residue (Moir, D. T., Mao, J.-i., Schumm, J. W., Vovis, G. F., Alford, B. L. and Taunton-Rigby, A. (1982) Gene 19, 127-138). Typically yeast strains, like CGY998, which have been transformed with this plasmid express approximately 0.2% of their cell protein as prochymosin. However, with such nonmutant yeast strains, only 1-2% of that prochymosin (0.002-0.004% of cell protein) is secreted into the medium.

The screening assay used in this example utilizes the facts that prochymosin is expressed and secrected from yeast strain CGY998 at this low level, and that the activity of this prochymosin can be assayed by a applying milk/agarose overlay to nutrient agar plates that have been used to grow colonies of such cells. Because this assay is fairly quantitative it is possible to identify cells that are secreting more chymosin activity amongst a background of cells that are already secreting some.

1. Mutagenesis

Cells from strain CGY998 were mutagenized with ethyl methane sulfonate according to the method of Sherman, et al (1981) supra. Aliquots of mutagenized cells were frozen at 70° C. in 40% (v/v) glycerol and thawed one at a time as they were required for screening experiments over a period of approximately 30 days.

2. Screening of Mutagenized Cells

Mutagenized cells were spread onto 9 cm nutrient agar plates that each contained approximately 25 ml of SD medium as described by Sherman, et al (1981) supra at a density that was empirically determined to yield approximately one hundred colonies per plate. After three days growth at 30° C., colonies of cells were removed from the surface of the plates by blotting with sterile 9 cm Whatman No. 1 filter paper discs. One filter paper replicate of each plate was saved for later recovery of mutant cells. Eight ml of a mixture of water, molten agarose (0.25% w/v), nonfat dry milk (5% w/v), $CaCl_2$ (5 mM), $NaPO_4$ (50 mM, pH 5.8), and pepstatin (20 mg/ml) were then poured over the surface of the plates and allowed to solidify. During an incubation period of four hours at room temperature opaque regions of clotted milk were observed in this overlay mixture that corresponded to regions of the plate which had absorbed secreted chymosin from the yeast colonies. Clots that were particularly intense or that formed particularly quickly were noted, and the corresponding yeast colonies were recovered from the filter paper replicates. These colonies were then subjected to a more exact quantitative assay for secreted chymosin activity, and those with secreted activities significantly higher than the starting strain were saved as putative supersecreting mutants. In all, 120,000 mutagenized colonies were screened, and 39 mutant strains were found to be supersecreting strains.

3. Analysis of mutant strains a. Secreted Activity. The secreteted activities of mutant strains wee measured by allowing a dense patch of cells to grow on an SD nutrient agar plate at 30° C. for three days. Cells from approximately 1 cm$^2$ of such a patch were scraped off the plate and resuspended in 0.4 ml of 50 mM $NaPO_4$ buffer (pH 5.8) at 0° C. for one hour. 0.1 ml of this suspension was then added to 1 ml of rehydrated nonfat dry milk and incubated with shaking at 30° C., noting the time required for the milk to coagulate. The secreted activity of a strain was calculated by the following formula:

$$\frac{835}{T \times K} = SA$$

where T=time of coagulation in minutes, K=density of 1:100 dilution of cell suspension as measured in a Klett colorimeter (0.6 cm path length, green filter #54), and SA=secreted activity expressed as units of chymosin activity per gram wet weight of cells ($\mu/g$). A unit of chymosin activity is defined as that amount of activity required to coagulate 10 ml of milk in 100 seconds. This formula assumes that one liter of cell suspension with a density of 50 as measured in a Klett colorimeter contains approximately one gram wet weight cells.

Generally this measurement was performed on three or four independent colonies of a putative mutant strain and the values obtained were averaged. A strain was classified as supersecreting if its average secreted activity (SA) was 0.50 $\mu/g$ or greater. (CGY 998 typically yields a secreted activity of between 0.15 $\mu/g$ and 0.25 $\mu/g$ in this assay). The highest secreted activity observed for a newly isolated mutant strain in this assay was 1.5 $\mu/g$. Most mutant strains had secreted activities between 0.6 and 0.9 $\mu/g$.

b. Dominance/Recessiveness. The supersecreting mutations in strains that met the above criterium were classified as to dominance or recessiveness by mating them to a nonmutant strain, CGY265 (a, ura3-52, leu1), and assaying the secreted activities of resulting diploids that retained the plasmid pCGS514. Fourteen of the thirty-nine strains tested formed diploids with secreted activities less than 0.25 μ/g and were classified as containing recessive mutations. The remaining strains all formed diploids with secreted activities between 0.25 μ/g and the secreted activity of the mutant parent and were classified as semi-dominant. No diploid strains were observed to have secreted activities higher than its supersecreting mutant parent.

c. Complementation of Recessive Mutations. Recessive mutations were classified into complementation groups by mating supersecreting mutant strains to supersecreting strains of the opposite mating type. (These had been derived by sporulating the diploids formed in step b. above). The supersecreting (ssc) mutations in two strains were said to complement if the resulting diploid had a secreted activity of less than 0.50 μ/g. Pairs of mutations that fail to complement presumably affect the same gene, and can be grouped together. In this way we have classified nine recessive supersecreting mutations into three complementation groups (ssc1, ssc2, and ssc3 —see Table 1). Individual alleles of mutations in each group have been assigned the designations ssc1-1, ssc1-2, etc. Five additional mutations fall into a fourth class that was complemented by all mutations that were available in strains of the opposite mating type and have been assigned an sscX designation. This fourth class may actually represent more than one complementation group and include mutations in more than one gene.

wise free of the residual effects of mutagenesis. This method can also be used to transfer various ssc mutations into a variety of different backgound strains in order to create new supersecreting strains with additional desired characteristics.

e. Failure of ssc1/ssc1 and ssc2/ssc2 diploids to sporulate. During the course of this work it was observed that diploid yeast strains that resulted from the mating of two strains each carrying a mutation in the ssc1 complementation group or two strains each carrying a mutation in the ssc2 complementation group would fail to form normal four spored asci upon incubation of sporulation medium. In fact, few if any spores will form in such diploids, indicating that uncomplemented ssc1 and ssc2 mutations lead to a defect in the sporulation pathway. This sporulation defect is exhibited by all strains carrying ssc1 or ssc2 mutations, including those which have been derived from original mutant strains by several rounds of outcrossing, thus enabling one to determine by a simple mating and sporulation test whether or not a particular strain contains an ssc1 or ssc2 mutation regardless of whether or not that strain is expressing and secreting prochymosin.

f. Multiply mutant supersecreting strains. Diploid strains formed by mating strains containing ssc mutations from different complementation groups were sporulated, and the resulting haploid strains were assayed for the ability to secrete prochymosin. In many cases haploid strains were derived that had secreted activities higher than either parents. Those with the highest secreted activities (up to 5.0 μ/g) were assumed

TABLE 1

| COMPLEMENTATION GROUP | ALLELE NUMBER | SECRETED ACTIVITY | SECRETED ACTIVITY IN DIPLOIDS[1] | | | |
|---|---|---|---|---|---|---|
| | | | X ssc1-1[2] (2180) | X ssc2-1 (1377) | X ssc2-2 (1036) | X ssc3-1 (746) |
| ssc1 | −1 | (1490) | 4540 | 265 | 369 | 216 |
| | −2 | (830) | 926 | 318 | 374 | 159 |
| | −3 | (630) | 602 | 340 | 333 | 223 |
| | −4 | (940) | 647 | 331 | 361 | 172 |
| | −5 | (700) | 746 | 472 | 398 | 161 |
| ssc2 | −1 | (1370) | 397 | 2049 | 715 | 200 |
| | −2 | (1120) | 477 | 624 | 531 | 212 |
| | −3 | (1100) | 636 | 838 | 720 | 304 |
| ssc3 | −1 | (710) | 373 | 304 | 374 | 1083 |
| sscX | −1 | (890) | 457 | 368 | 345 | 280 |
| | −2 | (700) | 459 | 486 | 356 | 173 |
| | −3 | (1070) | 374 | 310 | 307 | 189 |
| | −4 | (720) | 380 | 404 | 355 | 147 |
| | −5 | (1590) | 390 | 466 | 464 | — |
| WILD TYPE | | (150) | 350 | 331 | 315 | 237 |

[1]Secreted activities are expressed in units of milk clotting activity per gram wet weight of cells × 1000 (milliunits/g). In each case the secreted activity of each parent is listed in parentheses.
[2]This shorthand notation (X ssc1-1) means "when crossed to a tester strain containing the ssc1-1 mutation."

d. Transfer of ssc mutations away from mutagenized backgrounds. In order to remove isolated ssc mutations away from any residual mutations that may have been induced during mutagenesis, newly isolated mutant strains were crossed to nonmutagenized background strains of the opposite mating type and the resulting diploids were sporulated. Supersecreting progeny (those with secreted activities close to that of their mutant parent) from these crosses were identified and again crossed to nonmutant strains and sporulated. Supersecreting strains that were a result of this second round of outcrossing were assumed to contain the ssc mutation of the original mutant strain, but to be otherto contain mutations from both parents. In the case of strains believed to contain mutations of both the ssc1 and ssc2 complementation groups the presence of both mutations could be confirmed by the sporulation test described in step e.

g. Eliminating pCGS514 from Mutant Strains. Because plasmids such as pCGS514 do not always segregate into both daughter cells during cell division, mutant strains could be effectively "cured" of this plasmid simply by growing them for several generations on medium that did not provide selective pressure for the expression of the wild type URA3 gene carried by this plasmid. Normally this gene serves to complement the ura3-52 mutation in the mutant strains. Colonies that had been grown on a rich medium (YPD, Sherman, et al, (1981) supra) were tested one at a time for the ability to grow on minimal medium with and without supplementary uracil. URA− colonies were double checked for secreted chymosin activity (loss of the plasmid should also eliminate the prochymosin gene from these strains) and saved as cured versions of various mutant strains. These cured strains can be transformed with plasmids which contain other promoter/signal sequence/gene combinations.

Yeast strains prepared by the processes described above are exemplified by cultures now on deposit with the American Type Culture collection 12301 Parklawn Drive, Rockville, Md. These cultures are identified by Accession Number 20750, Strain Designation CGY1285 (mating type alpha, ura3-52, pep4-3, ssc1-1); Accession Number 20752, Strain Designation CGY1291 (mating type alpha, ura3-52, his4-29, pep4-3, ssc2-1); and Accession Number 20751, Strain Designation CGY1083 (mating type alpha, ura3-52, his4-27, pep4-3, ssc3-1) and were deposited by Collaborative Research, Inc., on Apr. 5, 1985. These three strains were chosen because each contains an example of a mutation from one of the three defined complementation groups of ssc mutations.

EXAMPLE 2

Improved secretion efficiency for bovine growth hormone

In this example it is shown that mutant yeast strains selected on the basis of their improved capacity for the secretion of prochymosin have utility in the production of a heterologous protein other than chymosin. Thus they may have general utility in the production of any protein that is to be secreted from yeast.

Figure 1B:
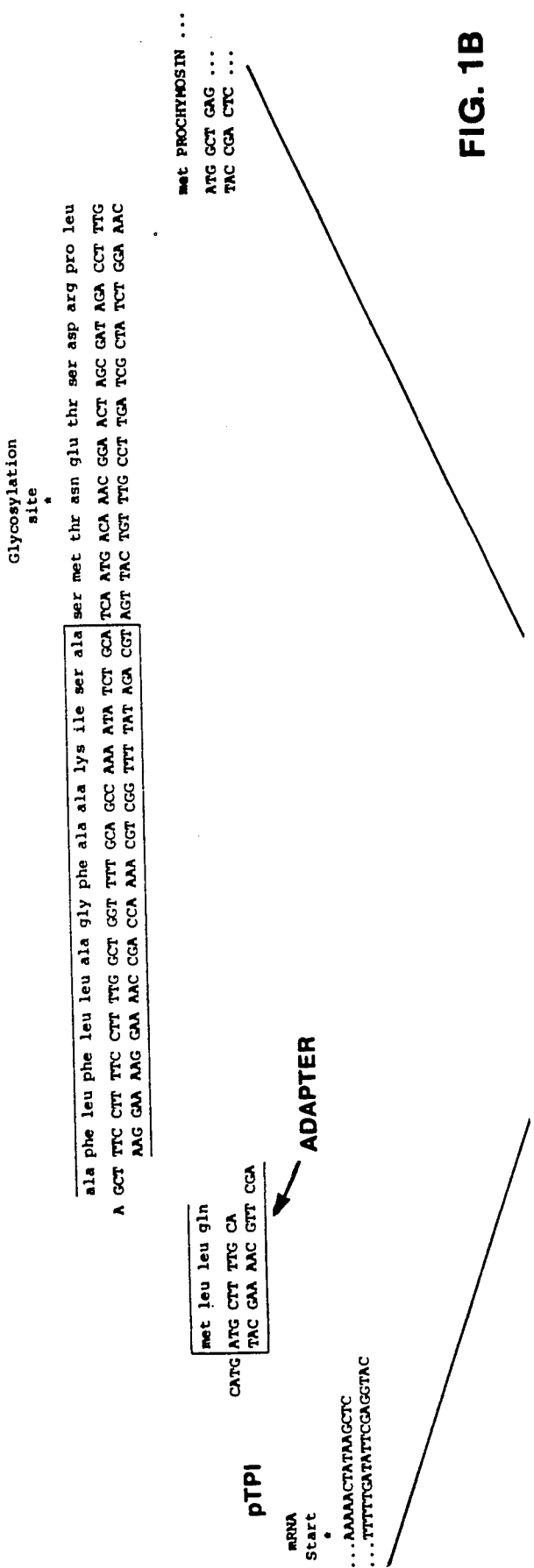

A recombinant DNA plasmid, designated pCGS447, identical to pCGS514 except that pCGS447 contains, in place of the approximately 2100 base pair pTPI-SUC2-prochymosin sequence (see FIGS. 1A and 1B), the complete coding sequence for bovine growth hormone (BGH) along with its amino terminal secretion signal or "pre" sequence fused to the promoter region of the yeast GAL1 gene (as described by Goff, et al (1984) supra) was used to transform four strains of yeast to uracil prototrophy by the LiCl method of Ito, et al, supra. One strain, CGY339 (mating type lapha, his4-27, ura3-52, pep4-3) was included as a wild type control strain that does not have a supersecreting phenotype (i.e. it is geneotypically SSC+). Two other strains, CGY1285 (mating type lapha, ura3-52, pep4-3, ssc1-1) and CGY1291 (mating type alpha, his4-27, ura3-52, pep4-1, ssc2-1), each contain a single mutation (ssc1-1 or ssc2-1) known to increase the amount of prochymosin secreted by these strains. The fourth strain, CGY1293 (mating type a, ura3-52, pep4-3, ssc1-1, ssc2-1) contains both these mutations and is known to secrete prochymosin more efficiently than strains containing either mutation alone. All three supersecreting strains were derived during the work described in Example 1 and had previously been cured of the plasmid pCGS514.

Isolated transformant colonies from each of these four strains were grown in patches on agar plates containing galactose as a carbon and energy source. (Growth on galactose is required for expression from the GAL1 promoter on pCGS447). Following a 96 hour incubation period, approximately 100 mg of cells from each transformed strain were scraped off these plates and suspended in 0.5 ml of 100 mM ammonium bicarbonate (pH 8.0). After the cells had been removed from this suspension by a brief centrifugation the supernatant portion were frozen and evaporated to dryness in vacuo.

The dried pellets were then resuspended 40 microliters of SDS sample buffer as described by Laemmli, U. D. and Favre, M. (1973) J. Mol. Biol. 80, 575–599 and subjected to immunoblot analysis as described by Towbin, H., Staehelin, T. and Gordon, J. (1979) Proc. Natl. Acad. Sci. USA 76, 4350–4354. The amount of bovine growth hormone (BGH) in each sample was estimated by comparison to purified standards on the same immunoblot and the amount of protein secreted per gram of cells calculated by dividing by the wet weight of the cells that had originally been present in each suspension. Results are presented in the following table:

| Background Strain | Secretion Genotype | Amount of BGH secreted |
| --- | --- | --- |
| CGY339 | SSC+ | 100 ng/g |
| CGY1285 | ssc1-1 | 1800 ng/g |
| CGY1291 | ssc2-1 | 200 ng/g |
| CGY1293 | ssc1-1, ssc2-1 | 2000 ng/g |

Clearly the ssc1-1 mutation is very effective at improving the secretion efficiency of bovine growth hormone from yeast. The effect of ssc2-1 is less dramatic, but still at least two fold the amount secreted in the absense of an ssc mutation, and the effect of both mutations in the same strain is approximately the sum of the effect of the two mutations individually.

EXAMPLE 3

Improved secretion efficiency for prourokinase

This example using prourokinase is a further demonstration that mutant yeast strains selected on the basis of their improved capacity for the secretion of prochymosin may have general utility in the production of any protein that is to be secreted from yeast.

Recombinant DNA plasmid pCGS696 is identical to pCGS514 except that pCGS696 contains, in place of the approximately 1300 base pair SUC2-prochymosin sequence (see table 1), the complete coding sequence for preprourokinase (prePUK) (UK Patent Application 2121050 "Preparation of Functional Human Urokinase Proteins" Heyneker, H. L., Holmes, W. E. and Vehar, G. A.) along with its amino terminal secretion signal or "pre" sequence as well as a 900 base pair DNA fragment from the yeast SUC2 gene including the transcription terminator region (Goff et al (1984) supra). Plasmid pCGS696 was used to transform four strains of yeast to uracil prototrophy by the LiCl method of Ito, et al, supra. One strain, CGY339 (mating type alpha, his4-27, ura3-52, pep4-3) was included as a wild type control strain that does not have a supersecreting phenotype (i.e. it is genotypically SSC+). Two other strains, CGY1285 (mating type alpha, ura3-52, pep4-3, ssc1-1) and CGY1291 (mating type alpha, his4-27, ura3-52, pep4-1, ssc2-1), each contain a single mutation (ssc1-1 or ssc2-1) known to increase the amount of prochymosin secreted by these strains. The fourth strain, CGY1463 (mating type alpha, ura3-52, leu 2-3,112, pep4-3, ssc1-1, ssc2-1) contains both these mutations and is known to secrete prochymosin more efficiently than strains containing either mutation alone. All three supersecreting strains were derived during the work described in Example 1 and had previously been cured of the plasmid pCGS514.

Isolated transformant colonies from each of these four strains were grown in patches on agar plates containing SD medium plus leucine and histidine. Following a 72 hour incubation period, approximately 200 to 400 mg of cells from each transformed strain were scraped off these plates and suspended in 0.5 ml 50 mM sodium phosphate (pH 7.0), 100 mM sodium chloride. Approximately 25 ul of each cell suspension was added to a well of a bovine plasminogen-rich, fibrin agarose plate (Brackman, P. (1967) Fibrinolysis, Scheltema and Holkema, Amsterdam, 1–124). The number of fibrinolytic units of prourokinase (PUK) in each sample was estimated by comparison of the fibrinolytic zone produced with that produced by purified standards on the same fibrin plate. The amount of PUK secreted per gram of cells was calculated by dividing by the wet weight of the cells that had originally been present in each suspension. Results are presented in the following table:

| Background Strain | Secretion Genotype | Amount of PUK secreted |
|---|---|---|
| CGY339 | SSC+ | not detectable |
| CGY1285 | ssc1-1 | 3.7 units/g |
| CGY1291 | ssc2-1 | 5.0 units/g |
| CGY1463 | ssc1-1, ssc2-1 | 6.6 units/g |

Clearly the ssc1-1 and ssc2-1 mutations are very effective at improving the secretion efficiency of PUK from yeast. The effect of both mutations in the same strain is greater than the effect of the two mutations individually.

While the specific embodiments of the invention have been shown and described, various modifications are possible. The present application gives specific examples of the production and secretion of prochymosin, bovine growth hormone and prourokinase from supersecreting mutants. However, other polypeptide gene products from mammalian or other sources such as human growth hormone (HGH), proinsulin, tissue plasminogen activator (TPA), alpha-1-antitrypsin and interleukin-2 supersecreting mutants.

We claim:

1. A method of obtaining a desired heterologous polypeptide product in high yield from supersecreting Saccharomyces yeast cells by collecting said product secreted from said yeast cells,
   said yeast cells being obtained by selecting a starting transformable yeast strain,
   causing said yeast strain to undergo mutagenesis and form mutant cells,
   said mutant cells being transformed to secrete a heterologous polypeptide,
   screening said mutant cells to determine those final cells which secrete said heterologous polypeptide in amounts greater than two times the amount secreted by said starting strain when so transformed, and culturing said final cells to obtain said high yields of heterologous polpeptide.

2. A method in accordance with the method of claim 1 wherein said yeast cells are transformed after mutagenesis.

3. A method in accordance with the method of claim 1 wherein said polypeptide is prochymosin.

4. A method in accordance with the method of claim 1 wherein said yeast is *Saccharomyces cerevisiae*.

5. A method in accordance with the method claim 1 wherein said starting transformed yeast strain comprises with DNA sequences for expression and secretion of said heterologous polypeptide.

6. A method in accordance with the method of claim 1 and further including the steps of curing said mutant cells obtained by screening and carrying out a second transformation step to introduce a heterologous DNA capable of causing secretion of a final desired heterologous polypeptide.

7. A method in accordance with the method of claim 6 wherein said heterologous polypeptide secreted by said mutant cells as a result of the first transformation is prochymosin and said final secreted polypeptide product as a result of said second transformation is bovine growth hormone.

8. A method in accordance with the method of claim 1 wherein said heterologous polypeptide is a mature protein.

9. A mutant Saccharomyces yeast strain which is a supersecreting strain for a final said heterologous polypeptide product and is obtained by.
   selecting a starting transformable yeast strain,
   causing said yeast strain to undergo mutagenesis and form mutant cells, said mutant cells being transformed to secrete a heterologous polypeptide, and screening said mutant cells to determine those final cells which secrete heterologous polypeptides in amounts greater than two times the amount secreted by said starting strain when so transformed.

10. A mutant yeast strain in accordance with claim 9 wherein said process includes transforming said mutant cells prior to mutagenesis.

11. A mutant yeast strain in accordance with claim 9 wherein said heterologous polypeptide is prochymosin.

12. Yeast strain American Type Culture Collection Accession Number 20750, Strain Designation CGY1285.

13. Yeast strain American Type Culture Collection Accession Number 20751, Strain Designation CGY1083.

14. Yeast strain American Type Culture Collection Accession Number 20752, Strain Designation CGY1291.

15. Yeast strain American Type Culture Collection Accession Number 20753, Strain Designation CGY998.

16. A method for selecting Saccharomyces yeast strains with increased secretory capabilities for secreting heterologous gene products, said method comprising:
   (a) selecting a transformable yeast strain,
   (b) mutagenizing said yeast strain,
   (c) transforming said mutagenized yeast strain with a heterologous DNA which confers upon said strain the ability to secrete a desired foreign polypeptide,
   (d) screening said mutagenized strain to determine those cells which secrete at least two fold higher amounts of said foreign gene product than non-mutated cells, and
   (e) isolating those mutant yeast cells which exhibit said at least two fold increase in the ability to secrete said foreign gene product.

17. A method in accordance with claim 16 wherein said gene product is prochymosin.

18. A method in accordance with claim 16 wherein the selected transformable yeast strain contains the gene for prochymosin.

19. A method in accordance with claim 16 wherein the selected transformable yeast strain contains DNA sequences for expression and secretion.

20. A method in accordance with claim 16 wherein the selected yeast strain is CGY998 American Type Culture Collection Accession Number 20753.

21. A method for selecting Saccharomyces yeast strains with increased secretory capabilities for secreting foreign gene products, said method comprising:
  (a) selecting a yeast strain containing the gene for prochymosin and DNA sequences for expression and secretion,
  (b) mutagenizing the yeast strain with ethyl methane sulfonate,
  (c) screening said mutagenized strain to determine those cells which secrete at least two fold higher amounts of prochymosin than a nonmutated cells, and
  (d) utilizing said last mentioned cells to produce a foreign protein.

22. A method in accordance with the method of claim 6 wherein said heterologous polypeptide secreted by said mutant cells as a result of the first transformation step is prochymosin and said final polypeptide product as a result of the second transformation step is prourokinase.

* * * * *